United States Patent [19]
Karol et al.

[11] Patent Number: 5,849,925
[45] Date of Patent: Dec. 15, 1998

[54] BIS-1,3,4-THIADIAZOLE COMPOUNDS AND LUBRICATING COMPOSITIONS CONTAINING SAME

[75] Inventors: Thomas J. Karol, Norwalk; Ronald J. Tepper, Fairfield, both of Conn.

[73] Assignee: R. T. Vanderbilt Co., Norwalk, Conn.

[21] Appl. No.: 764,942

[22] Filed: Dec. 13, 1996

[51] Int. Cl.$^6$ ........................ C07D 285/12; C10M 133/38
[52] U.S. Cl. ............................................ 548/142; 252/47.5
[58] Field of Search ............................. 548/142; 252/47.5

[56] References Cited

U.S. PATENT DOCUMENTS

| | | | |
|---|---|---|---|
| 4,128,510 | 12/1978 | Richwine | 548/142 |
| 4,584,114 | 4/1986 | Gemmill et al. | 252/47.5 |
| 4,761,482 | 8/1988 | Karol | 548/142 |
| 5,177,212 | 1/1993 | Karol et al. | 548/142 |

*Primary Examiner*—Robert Gerstl
*Attorney, Agent, or Firm*—Baker & Botts LLP

[57] ABSTRACT

Disclosed are novel compounds prepared by reacting two moles of 2,5-dimercapto-1,3,4-thiadiazole and one mole of a hydrocarbon compound selected from terpenes, aryl compounds and aliphatic compounds which may be substituted by oxygen or oxygen containing groups. The hydrocarbon compound forms a bivalent radical linking together the two 2,5-dimercapto-1,3,4-thiadiazoles. The compounds are effective extreme pressure agents when incorporated into lubricating compositions.

18 Claims, No Drawings

BIS-1,3,4-THIADIAZOLE COMPOUNDS AND LUBRICATING COMPOSITIONS CONTAINING SAME

SPECIFICATION

BACKGROUND OF THE INVENTION

The present invention concerns novel bis-1,3,4-thiadiazole compounds derived from terpene, arylene and alkylene compounds. Another aspect of the invention concerns lubricating compositions containing bis-1,3,4-thiadiazole compounds which impart extreme pressure properties to said compositions.

Additives known as extreme pressure agents are employed to increase the load carrying capacity of lubricants. The extreme pressure agents promote the formation of a surface film and thereby prevent wear, welding and abrasion of the contacting surfaces. When used in lubrication of internal combustion engines, the mechanical efficiency enhanced by decreased friction loss further results in decreased fuel consumption and energy savings.

It is known that certain terpene derivatives of 1,3,4-thiadiazole possess antiwear and antioxidant properties. U.S. Pat. No. 4,761,482 and U.S. Pat. No. 5,177,212 disclose 1,3,4-thiadiazole compounds having a monosubstituent terpene residue. The latter also discloses bis-1,3,4-thiadiazole compounds of alkylated benzene.

Surprisingly, it has been now discovered that certain novel bis-1,3,4-thiadiazole derivatives of terpene compounds, arylene compounds and alkylene compounds impart extreme pressure properties to lubricating compositions.

SUMMARY OF THE INVENTION

In accordance with the invention, there are provided novel bis-1,3,4-thiadiazole compounds having the structural formula

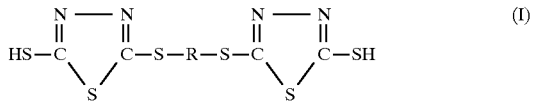

wherein R represents a divalent arylene radical having 6 to 12 carbon atoms, arylene radical having alkyl, oxygen or oxygen containing substituent groups; alkylene radical having oxygen or oxygen containing substituent groups; a divalent radical derived from terpenes, oxygenated terpenes or mixtures thereof.

Another aspect of the invention concerns improved oil-based lubricating compositions comprising a major amount of base oil and an effective amount to impart extreme pressure properties to said compositions, of a bis-1,3,4-thiadiazole compound of formula I.

A further aspect of the invention concerns a method for protection of metal surfaces from wear by applying improved lubricating compositions, the improvement of which consists of adding to the composition an effective amount of a bis-1,3,4-thiadiazole compound characterized by the structural formula I.

DESCRIPTION OF SPECIFIC EMBODIMENTS

The novel compounds of the invention are prepared by reacting two moles of 2,5-dimercapto-1,3,4-thiadiazole and one mole of a hydrocarbon compound which can form a bivalent radical linking the two 2,5-mercapto-1,3,4-thiadiazole (hereinafter DMTD) molecules at the sulfur of the mercapto groups. The hydrocarbon reactant can be a terpene, aryl compound or aliphatic compound.

In the case of terpene compounds, the sulfur of the mercapto group attaches to two types of unsaturation. The two reaction sites are either double bonds of the substituent groups and within the ring structure or unsaturation through a ring opening afforded by the strained bridged ring system. Alternately, a free hydroxy group on the terpene will enter into the reaction with the mercaptan group and will yield water through dehydration. Similarly, aliphatic compounds having ethylene unsaturation will attach to the sulfur of the mercaptan group at the double bonds. In the case of aryl compounds, the sulfur of the mercapto group attaches to the alpha, beta-unsaturated substituent of the aryl ring by an addition reaction. It can also attach to a substituent group having alpha, beta-unsaturation or to a hydroxy group.

The hydrocarbon compounds from which the compounds of the invention can be derived are selected from terpenes, aryl compounds and aliphatic compounds having oxygen or oxygen containing groups.

Terpenes are derivatives of isoprene and are classified according to the number of isoprene units in their carbon skeletons. The terpene compounds useful to this invention are acyclic or open chain, monocyclic, bicyclic or tricyclic. Commercial terpenes are generally isomeric mixtures and may contain saturated or partially saturated isomers. Various mixed terpenes and technical grade terpenes are available commercially. Useful terpenes, among others, are alpha-pinene, limonene, terpinolene, 1,4-cineole, 1,8-cineole, camphene, alpha-terpinene, gamma-terpinene and the like. Other terpenes contemplated herein are oxygenated terpenes as for example alpha-and gamma-terpineol, linalool, terpin, phorone and the like.

The arylene compounds useful to the invention may be substituted by pendant oxygen and oxygen containing groups, alkylene and alkyl groups containing up to 6 carbon atoms. Examplary compounds are, among others, dihydroquinone, diisopropenylbenzene and the like.

Aliphatic compounds that can be used to link the two 1,3,4-thiadiazole molecules may contain hydrocarbyl, oxygen or oxygen containing substituent groups. Preferred are alkylene compounds having 1 to 6 carbon atoms in the backbone. The aliphatic compounds may be straight chain or branched chain.

Particularly preferred are alkylene compounds having on the backbone substituents represented by the structural formula II.

wherein n=0 to 14, $R^1$ is hydrogen or methyl, $R^2$ is hydrogen, branched or straight chain alkyl having 1 to 20 carbons.

The alkylene compounds may have one or more substituents that are selected from those represented by the formula II or other oxygen containing groups such as oxo, carbonyl, alkoxy and the like. Such compounds include, among others, glyoxal, alpha, beta-unsaturated ketones, phorone, allyl glycidyl ether, allyl methacrylate and the like.

The bis-1,3,4-thiadiazole derivatives of the invention are useful as additives for lubricants. The compounds possess extreme pressure properties.

The lubricating compositions contemplated herein include lubricating oils and lubricating greases containing a major amount of base oil. The base oil may be selected from naphthenic, aromatic, paraffinic, mineral and synthetic oils. The synthetic oils may be selected from, among others, alkylene polymers, polysiloxanes, carboxylic acid esters and polyglycol ethers.

The amount of the thiadiazole additive required to be effective for imparting extreme pressure characteristics to lubricating compositions may range from about 0.01 to 10.0 percent of the lubricating composition. The preferred range is about 0.1 to 5.0 percent of the additive based on the weight of the lubricating composition.

To facilitate incorporation into the lubricating composition, the bis-1,3,4-thiadiazoles can be diluted with a diluent. For producing an additive in liquid form, preferred are diluents that have little effect on the dropping point of the grease products. Useful diluents, among others, are butoxytriglycol, propylene glycol, triethanolamine, butanol, polyol esters, aromatic petroleum oil and the like.

Lubricating oils may require a suspension agent for incorporation of bis-1,3,4-thiadiazoles into the composition. The suspension agent may be selected from dispersants or detergents as for example, among others, polyisobutylsuccinimide, calcium alkylsulfonates, calcium arylsulfonates and polyisobutyl succinate.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes.

Depending on the intended use of the lubricant, other functional additives may be added to enhance a particular property of the lubricant. The lubricating compositions may further contain other known additives, among others, antiwear additives, such as zinc dialkyldithiophosphates and zinc diaryldithiophosphates. Particularly preferred are zinc dialkyldithiophosphates having up to 8 carbon atoms in the alkyl group. Other additives include antioxidants such as alkylated diphenylamines, alkylphenols and bisalkylphenols. Particularly preferred are dialkyldiphenylamines having 8 to 9 carbons in the alkyl group and alkylphenols having 1 to 6 carbon atoms in the alkyl group. Preferred friction modifiers are molybdenum compounds, such as molybdenum dihydrocarbyl dithiocarbamates, molybdenum dihydrocarbyl dithiophosphates, molybdenum dihydrocarbyldithiophosphates and molybdates derived from cocodiethanolamide or cocomono-glyceride. Molybdenum dialkyldithiocarbamates having 2 to 8 carbon atoms in the alkyl group and molybdenum dialkyldithiophosphates having 6 to 16 carbon atoms in the alkyl group are particularly preferred. Extreme pressure additives may be selected from metal dihydrocarbyldithiocarbamates. Preferred are bismuth naphthenate, zinc dialkyldithiocarbamates, antimony dialkyldithiocarbamates and bismuth dialkyldithiocarbamates, particularly alkyl derivatives having 2 to 8 carbons in the alkyl group. Metal passivators may be selected from benzotriazoles and tolutriazoles and their alkylamine, diphenylamine, alkylated diphenylamine derivatives, and derivatives of 2,5-dimercapto-1,3,4-thiadiazoles as for example 2,5-dialkylthio-1,3,4-thiadiazole. Useful rust ihibitors include, among others, dodecylsuccinic anhydride, its mono propylene glycol ester and the like.

The following examples are given for the purpose of further illustrating the invention. All percentages and parts are based on weight unless otherwise indicated.

EXAMPLE 1

A reactor equipped with a condenser and stirrer was charged with 2,5-dimercapto-1,3,4-thiadiazole (DMTD), 1308 g (8.72 moles), dimethylketone, 650 ml, and polyol ester (4 cst, Hatcol®1510 manufactured by Hatco Co.), 500 g. m-Diisopropenylbenzene, 690 g (4.36 moles) was added and the reaction was heated to reflux at about 70° to 73° C. for about one hour. The reaction was stripped of solvent at 125° C. with aspirator vacuum. The reaction product, bis-DMTD of m-di-isopropenylbenzene was diluted with polyol ester diluent, 1500 g. The structure of the reaction product was determined by infrared spectrum analysis and is given in Table I.

EXAMPLE 2

A reactor equipped with a stirrer and Dean Stark condenser was charged with DMTD, 96.425 g (0.642 moles), beta-terpineol, 49.5 g (0.32 moles) and n-butanol, 46 ml. The reaction was heated to 110° C. for about one hour until all water of reaction was collected. The structure of the reaction product is given in Table I.

EXAMPLE 3

A reactor equipped with a condenser and stirrer was charged with DMTD, 88.635 g (0.590 moles), alpha-pinene, 40.2 g (0.295 moles) and n-butanol, 40 ml. The reaction was heated at 120° to 131° C. for about one and half hours. The yield was 132.7 g of brown oil. The structure of the oily product was determined by infrared spectrum analysis and is given in Table I.

EXAMPLE 4

A reactor equipped with a condenser and stirrer was charged with DMTD, 112.195 g (0.747 moles), d-limonene, 50.9 g (0.374 moles) and n-butanol, 50 ml. The reaction was heated at 115° to 126° C. for about an hour and half. The structure of the reaction product was determined by infrared spectrum analysis and is given in Table I.

EXAMPLE 5

The reaction described in Example 4 was repeated by using a terpene mixture (Dipentene® manufactured by Aldrich Co.) instead of d-limonene. The reaction product was diluted with propylene glycol to make up 50 percent solution.

EXAMPLE 6

A reactor was equipped with a stirrer and a hydrogen sulfide trap to absorb any by-product formed. The reactor was charged with DMTD, 98.8 g (0.658 moles), phorone, 45.7 g (0.331 moles) and butoxytriglycol, 65.1 g. The reaction was heated at 90° to 101° C. for about one hour. The structure of the reaction product was determined by infrared spectrum analysis and is given in Table I.

EXAMPLE 7

The reaction described in Example 6 was repeated by using a terpene mixture (Acintene® DP 738 manufactured by Arizona Chemical Co.) instead of phorone. The product contained 30% butoxytriglycol diluent.

EXAMPLE 8

A reactor containing a magnetic stirrer was charged with DMTD, 37.05 g (0.247 moles), benzoquinone, 13.3 g (0.123 moles) and butoxy triglycol, 34.9 g. The mixture was heated at 101° to 119° C. with some evolution of hydrogen sulfide by-product. The structure of the reaction product was determined by infrared spectrum analysis and is given in Table I.

EXAMPLE 9

The reaction described in Example 8 was repeated by using 0.5 equimolar amount of glyoxal instead of benzoquinone based on DMTD. The glyoxal derivative was then reacted with n-butanol. The structure of the reaction product is given in Table I.

EXAMPLE 10

A reactor equipped with a stirrer and Dean-Stark condenser was charged with 40% glyoxal, 81.6 g (0.562 moles), triethylene glycol monobutyl ether, 231.9 g (1.124 moles), 97% sulfuric acid, 0.4 g (0.004 moles) and heptane, 40 ml. The reaction was heated until 56.5 g of reaction water was obtained. The reactor was charged with 96% DMTD, 171.9 g (1.129 moles) and was heated to 140° C. with some evolution of hydrogen sulfide by-product. The structure of the reaction product is given in Table I.

TABLE I

| Example | Structure of Bis-1,3,4-thiadiazole compounds |
|---|---|
| 1 | HS-C(N=N)S-C(CH₃)₂-S-C-[phenyl]-C-S-C(CH₃)₂-S-C(N=N)-SH |
| 2, 3 & 4 | HS-C(N=N)S-C(CH₃)₂-S-C-[CH₃-phenyl]-S-C(N=N)-SH |
| 6 | HS-C(N=N)S-C(CH₃)₂-S-C-CH₂-C(=O)-CH₂-C(CH₃)₂-S-C(N=N)-SH |
| 8 | HS-C(N=N)S-C-S-[cyclohexanedione]-S-C(N=N)-SH |
| 9 | HS-C(N=N)S-C-S-CH(O-C₄H₉)-CH(O-C₄H₉)-S-C(N=N)-SH |
| 10 | HS-C(N=N)S-C-S-C(OR³)-C(OR³)-S-C(N=N)-SH | wherein R³ is —CH₂—CH₂O(CH₂CH₂O)₂C₄H₉

EXAMPLE 11

Extreme Pressure Tests

The load carrying properties of a lithium grease containing the compounds of the invention were tested essentially acording to the method described in ASTM D 2596-87. The test was conducted at a rotating speed of 1800 rpm and 54.40° C. The test samples 1, 3, 4 and 5 were subjected to a series of tests of 10 second duration at increasing loads until welding of the balls occured. The weld point measured in kgf indicates that the extreme pressure level of the grease has been exceeded. The samples tested are compiled in Table II. The base grease used was lithium 12-OH stearate grease manufactured by Witco Co. or a Li complex grease manufactured by Chem Tool Co.

Test sample 2 was formulated in polyol ester oil (Castrol 5000 manufactured by Castrol Co.) and together with control, test sample 6, tested by ASTM D-2783.

The results compiled in Table II demonstrate that the compounds of the invention possess extreme pressure properties.

TABLE II

| | | Extreme Pressure Test | | | |
|---|---|---|---|---|---|
| Sample | Base | Active Ingredient | Mass Percent | Weld Point, kgf | Wear at 40 kg, 1 hr., mm |
| 1 | Li-2OH | Prod. of Ex. 5 | 4.0 | 315 | 0.60 |
| 2 | Polyol ester | Prod. of Ex. 1 | 3.0 | 400 | — |
| 3 | Li complex | Prod. of Ex. 7 | 2.14 | 400 | 0.79 |
| 4 | Li-12OH | — | — | 160 | 0.58 |
| 5 | Li Complex | — | — | 160 | 0.63 |
| 6 | Polyol ester | — | — | 160 | — |

The above embodiments have shown various aspects of the present invention. Other variations will be evident to those skilled in the art and such modifications are intended to be within the scope of the invention as defined by the appended claims.

What is claimed is:

1. A bis-1,3,4-thiadiazole compound having the structural formula

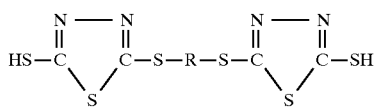

wherein R represents a divalent radical derived from mixed terpenes.

2. A bis-1,3,4-thiadiazole compound having the structural formula

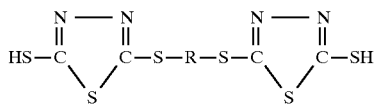

wherein R represents a divalent radical derived from oxygenated terpenes.

3. A bis-1,3,4-thiadiazole compound having the structural formula

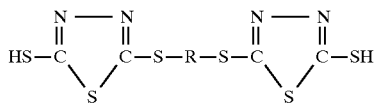

wherein R represents a divalent radical derived from limonene.

4. A bis-1,3,4-thiadiazole compound having the structural formula

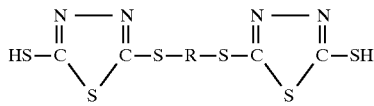

wherein R represents a divalent radical derived from glyoxal.

5. A lubricating composition comprising a major portion of an oil of lubricating viscosity and a minor extreme pressure imparting amount of a bis-1,3,4-thiadiazole compound selected from the group consisting of compounds having the structural formula

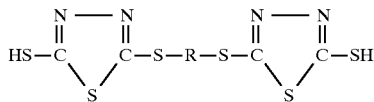 (I)

wherein R represents a divalent arylene radical having oxygen or oxygen containing substituent groups, alkyl and alkylene groups having up to 6 carbon atoms; alkylene radical having oxygen or oxygen containing substituent groups; and a divalent radical derived from terpenes, oxygenated terpenes or mixtures thereof.

6. A lubricating composition according to claim 5 which contains a thickener.

7. A lubricating composition according to claim 5 wherein the R group in the bis-1,3,4-thiadiazole compound is derived from mixed terpenes.

8. A lubricating composition according to claim 5 wherein the R group in the bis-1,3,4-thiadiazole compound is derived from oxygenated terpenes.

9. A lubricating composition according to claim 5 wherein the bis-1,3,4-thiadiazole compound is present in an amount ranging from about 0.01 to 10.0 percent of the lubricating composition.

10. A lubricating composition according to claim 5 wherein the R group in the bis-1,3,4-thiadiazole compound is a bivalent arylene radical having alkyl, alkylene and oxygen substituent groups.

11. A lubricating composition according to claim 5 containing 0.01 to 10.0 percent of bis 1,3,4-thiadiazole compound wherein R is presented by limonene radical.

12. A lubricating composition according to claim 5 wherein the R group in the bis-1,3,4-thiadiazole compound is a divalent alkylene radical having oxygen or oxygen containing substituent groups.

13. A lubricating composition comprising a major portion of an oil of lubricating viscosity and a minor extreme pressure imparting amount of a bis-1,3,4-thiadiazole compound selected from the group consisting of compounds having the structural formula

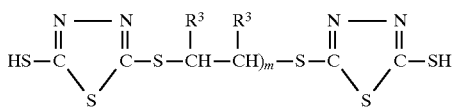

wherein m=1 to 3 and $R^3$ is represented by the structural group

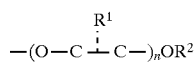

and n=0 to 14, $R^1$ is hydrogen or methyl and $R^2$ is hydrogen or branched or straight chain alkyl having 1 to 20 carbon atoms.

14. A lubricating composition according to claim 13 wherein $R^3$ is represented by the structural group

15. A lubricating composition according to claim 13 wherein $R^3$ is derived from butoxytriglycol.

16. A method for protecting metal surfaces from wear which comprises contacting the surfaces with a lubricating composition comprising a major amount of base oil of lubricating viscosity, the improvement of which consists of adding to the oil a minor extreme pressure imparting amount of an additive selected from the group of compounds having the structural formula

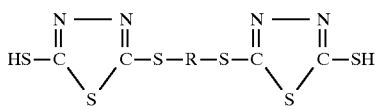

wherein R represents a divalent arylene radical having oxygen or oxygen containing substituent groups, alkyl and alkylene groups having up to 6 carbon atoms; alkylene radical having oxygen or oxygen containing substituent groups, and a divalent radical derived from terpenes, oxygenated terpenes or mixtures thereof.

17. A method according to claim 16 wherein the additive is admixed with a diluent prior to addition to the base oil.

18. A method according to claim 16 wherein the lubricating composition contains a thickener.

* * * * *

UNITED STATES PATENT AND TRADEMARK OFFICE
CERTIFICATE OF CORRECTION

PATENT NO. : 5,849,925
DATED : December 15, 1998
INVENTOR(S) : Karol et al.

It is certified that error appears in the above-indentified patent and that said Letters Patent is hereby corrected as shown below:

Column 1, line 5: "SPECIFICATION" should be deleted

Coumn. 2., line 33: "Examplary" should read --Exemplary--

Column 3, line 38: "cocomono-glyceride" should read --cocomonoglyceride--

Column 4., line 16: "one and half hours" should read --one and one-half hours--

Column 4., line 26: "half." should read --a half.--

Column 5., Table 1: "Bis-" should read -bis- --

Column 5., Table 1: the chemical structure of Example 1

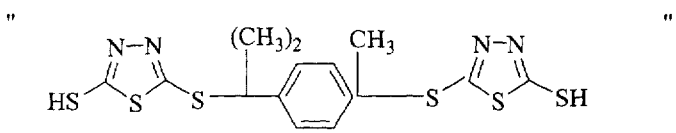

should read

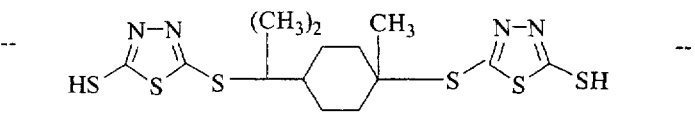

Column 6, Table 2: The first Base, "Li-2OH" should read --Li-12OH--

UNITED STATES PATENT AND TRADEMARK OFFICE
CERTIFICATE OF CORRECTION

PATENT NO. : 5,849,925
DATED : December 15, 1998
INVENTOR(S) : Karol et al.

It is certified that error appears in the above-indentified patent and that said Letters Patent is hereby corrected as shown below:

Column. 8, line 7: "presented" should read -- represented --

Signed and Sealed this

Tenth Day of April, 2001

Attest:

NICHOLAS P. GODICI

*Attesting Officer*     *Acting Director of the United States Patent and Trademark Office*